(12) United States Patent
Johe (10) Patent No.: US 9,572,807 B2
(45) Date of Patent: Feb. 21, 2017

(54) PROTOCOLS FOR TREATMENT OF MAJOR DEPRESSIVE DISORDER (MDD)

(71) Applicant: NEURALSTEM, INC., Germantown, MD (US)

(72) Inventor: Karl K. Johe, Sunny Isles, FL (US)

(73) Assignee: Neuralstem, Inc., Germantown, MD (US)

(*) Notice: Subject to any disclaimer, the term of this patent is extended or adjusted under 35 U.S.C. 154(b) by 0 days.

(21) Appl. No.: 14/740,070

(22) Filed: Jun. 15, 2015

(65) Prior Publication Data

US 2015/0359792 A1    Dec. 17, 2015

Related U.S. Application Data

(60) Provisional application No. 62/012,880, filed on Jun. 16, 2014.

(51) Int. Cl.
*A61K 31/496* (2006.01)
*A61K 31/444* (2006.01)

(52) U.S. Cl.
CPC .......... *A61K 31/496* (2013.01); *A61K 31/444* (2013.01)

(58) Field of Classification Search
CPC ............................ A61K 31/496; A61K 31/444
See application file for complete search history.

(56) References Cited

U.S. PATENT DOCUMENTS

| 7,560,553 B1 * | 7/2009 | Kelleher-Andersson | G01N 33/5008 544/365 |
| 8,030,492 B2 | 10/2011 | Kelleher-Andersson et al. | |
| 8,362,262 B2 | 1/2013 | Kelleher-Andersson et al. | |

OTHER PUBLICATIONS

Zimmerman, "Derivation of a definition of remission on the Montgomery-Asberg depression rating scale corresponding to the definition of remission on the Hamilton rating scale for depression", Journal of Psychiatric Research 38 (2004) 577-582.*
Prichep, "QEEG Profiles of Psychiatric Disorders", Brain Topography, vol. 4 (4), 1992, pp. 249-257.*
International Search Report and Written Opinion for PCT/US2015/035859, mailed Sep. 11, 2015, 6 pages.
Lotrich et al., "Brain-Derived Neurotrophic Factor Serum Levels and Genotype: Association with Depression during Interferon-α Treatment," Neuropsychopharmacology (2013) 38:985-995.
Neuralstem Inc., "Multiple-Dose Pharmacokinetics (PK), and Pharmacodynamic (PD) Effect of NSI-189 Phosphate in Depression Patient Subjects," ClinicalTrials.gov, Sep. 9, 2013, 3 pages, retrieved on Aug. 4, 2015 from the Internet. <URL: http://web.archive.org/web/20140306234759/http://clinicaltrials.gov/ct2/show/NCT01520649?>, entire document.

* cited by examiner

*Primary Examiner* — Sahar Javanmard
(74) *Attorney, Agent, or Firm* — Morrison & Foerster LLP

(57) ABSTRACT

Although it is known that certain benzylpiperazine-aminopyridines or open chain forms thereof are effective in stimulating neural growth in in vitro tests, it has now been surprisingly found that administering these compounds in a dosage range of 10 mg/day-130 mg/day over 25-35 days is effective in treating Major Depressive Disorder (MDD) such that statistically significant results can be obtained with samples of only six subjects.

10 Claims, 6 Drawing Sheets

Figures 1A, B and C

Figures 2A, B and C

Figures 3A, B and C

Figures 4A, B and C

Figures 5A and B

Figures 5C and D

PROTOCOLS FOR TREATMENT OF MAJOR DEPRESSIVE DISORDER (MDD)

CROSS-REFERENCE TO RELATED APPLICATIONS

This application claims priority from U.S. provisional application 62/012,880 filed 16 Jun. 2014. The contents of this document is incorporated herein by reference.

TECHNICAL FIELD

The invention relates to treatment for depression, in particular Major Depressive Disorder (MDD). The treatment involves administering specifically effective amounts of certain benzylpiperazine-aminopyridine compounds and the comparable open-chain forms over a period of approximately one month.

BACKGROUND ART

U.S. Pat. No. 8,362,262 is representative of a family of granted U.S. patents that describe low molecular weight compounds that are capable of stimulating neuronal growth. The description contained in these patents indicates that one of the indications for which these compounds may be useful is the treatment of depression. This disclosure is based on the theory that depression may be, in fact, a symptom of inadequate neuronal growth. No information is, however, supplied with regard to appropriate dosage or protocol design in humans, nor are there specific recommendations with regard to mode of administration.

It has now been found that two compounds in particular are effective in a defined dose range when administered orally to treat MDD and the effect is so dramatic and so long lasting that even cohorts as small as six subjects provide highly statistically significant results showing dramatic improvement in the MDD condition of the subjects as measured by recognized tests.

DISCLOSURE OF THE INVENTION

Thus, in one aspect, the invention is directed to a method to treat major depressive disorder (MDD) in a human subject, which method comprises administering to said subject an amount of a compound of formula (1) or formula (2)

in the amount of 10 milligrams-130 milligrams per day (mg/day). The compounds can be administered orally in gelatin capsules. Administration is over at least 25 days.

In another aspect, the invention is directed to oral formulations designed to provide specific dosages.

MODES OF CARRYING OUT THE INVENTION

The invention provides a highly successful protocol for treating MDD in humans by administering, orally, for example, either once or twice or thrice a day a dosage range between 10 mg/day and 130 mg/day, preferably between 30 mg/day and 100 mg/day. Preferably the range is 40 mg/day-80 mg/day. While administration once or twice a day is preferred, by diminishing the amounts of compound in the formulation, more frequent dosage can be used; thus if a total of 87 mg/day is to be administered, individual dosages of 29 mg would be used for administration three times a day; if the total dosage is 48 mg per day, then each dosage for administration three times a day would be 16 mg. Generally, less frequent administration is preferred, but a three-times-per-day regime is also sometimes helpful in view of the ability to correlate administration with meals.

A variety of specific protocols can be workable within the parameters set forth. Essentially, administration one to three times per day of an oral formulation with the total amount administered per day in the range of 10 mg-130 mg, or preferably 40 mg-90 mg is used. It should be evident that if higher amounts are to be administered, then more frequent dosage per day with a lower per dose amount would be preferred. Thus, if 90 mg per day is to be administered it may be preferable to administer this three times per day at 30 mg per dose or two times a day at 45 mg/dose, rather than to employ a single bolus dose of 90 mg. In general, it is preferable to limit the amount per dose to 50 mg or less, preferably 40 mg or less, or 30 mg or less.

While a variety of administration routes may be employed, including injection intramuscularly or intravenously, it is clearly preferred to dose orally if at all possible. In this case, oral dosage is indeed possible, and if oral dosage is possible it is clearly preferred. A variety of formulations for oral administration may be used, including delayed-release formulations, in various forms such as tablets, capsules, powders, liquids, and the like. The formulation is conveniently in gelatin capsules, although those who have difficulty in swallowing may prefer a liquid formulation, which is also suitable for administering the compounds of the invention. While the examples below illustrate a clinical study involving hospitalized patients, in general practice, the compounds of the invention can be self-administered by human subjects in their own environments such as at home or at work.

The formulations may include any formulation suitable for oral administration such as capsules, tablets, syrups, and the like. Standard fillers may be used or formulations that provide instant availability of the active compound may be employed.

While it is convenient to divide the dosages evenly if more than one dose per day is to be administered, this is not a prerequisite, and differing amounts can be administered at each dose provided the daily range of compound administered is employed. Similarly, it is not necessary to administer an identical dose on each day.

Typically, the duration of the protocol is roughly one month, preferably 25-35 days or any number of days in between. Longer periods of administration are also within the scope of the invention, e.g., 12 weeks or 3 months. In one protocol, a 3-month on, 3-month off regime is used. It is possible to formulate protocols where one or two days is skipped during the overall period as long as the general parameters of the dosage regime are maintained.

The success of the treatment can be measured in a number of ways, including, for example, a quantitative electroencephalogram (qEEG) where individuals treated with the compounds of the invention show improvements by an increase of high frequency $\alpha$ (HF$\alpha$) waves in the qEEG.

Other measures include the Montgomery-Asberg Depression Rating Scale (MADRS) and/or the Clinician Global Impression-Improvement Scale (CGI-I), and/or the Symptoms of Depression Questionnaire (SDQ), and/or the Cognitive and Physical Functioning Questionnaire (CPFQ).

The results obtained show improvements during the period of administration, at the end-point, which is the last day of dosage or the day thereafter, in one or more or all of these measures when subjects are administered dosages within the required range. The improvement is maintained as shown by evaluation done one month, for example, after the end of the protocol or longer. Evaluation should be done after at least one month subsequent to termination of dosing. Evaluation at later times is also contemplated.

In the examples below, the compound of formula (1) was used in a Phase 1B randomized, double-blind, placebo-controlled, multiple-dose escalation study. Depressed patients on the various dosages illustrated showed clinically meaningful reductions in depressive and cognitive systems across all measures against placebo. These improvements persisted throughout a follow-up period extending for an additional month and a half after the administration was ended.

The following examples are offered to illustrate but not to limit the invention.

EXAMPLE 1

Responses Measured by qEEG

A double-blind, placebo-controlled, multiple-ascending-dose study employing the compound of formula (1) was performed in patients with symptomatic MDD. Twenty-four subjects were recruited, with their diagnosis and illness severity confirmed through an independent, remote SAFER interview (Targum, S. D., et al., *CNS Neurosci. Ther*. (2008) 14:2-9) from the Massachusetts General Hospital (MGH) Clinical Trials Network and Institute (CTNI) raters. Each patient underwent a screening for eligibility (Day −37 to Day −6 or −3) and eligible patients were admitted into the unit on Day −5 to complete their wash-out and be reconfirmed for eligibility and for baseline assessments. The patients received daily dosing of formula (1) or placebo for 28 days starting on Day 1 and were followed for safety, pharmacokinetics (PK) and pharmacodynamics (PD) until discharge. At the conclusion of in-house dosing (Day 28), patients remained in the unit for up to 3 additional days, at the psychiatrist's discretion. On Day 35 (±3), Day 42 (±3), Day 49 (±3) and Day 70 (±3) outpatient follow-up visits took place. Patients returned to the unit for extensive follow-up on Day 56 (±3) and Day 84 (±3) (End-of-study).

The subjects were randomized into four groups of 6 patients each to receive 40 mg of formula (1) per dose administered orally in gelatin capsules once daily, twice daily or three times daily to provide 40 or 80 or 120 mg daily of formula (1) or placebo for 28 days. Each cohort included at least 3 female subjects. In this example, qEEG was used to characterize pharmacodynamic effects.

In addition to safety, pharmacokinetic and the behavioral ratings scales described in Example 2, qEEG measurements were obtained 6 hours post-dose on Days 14 and 28 for 20 minutes at rest. EEGs were recorded using 19-standard International 10/20 System scalp locations plus electromyography (EMG) and eye movement monitoring. Digital EEGs recorded using Cadwell Laboratories instrumentation, were reviewed to identify the presence of physiological and instrumentation prior to analyses. Artifacts were removed from EEG files manually by an experienced technologist. Epochs of EEG data are submitted to power spectral analyses using Brain Vision Analyzer software.

Safety EEGs recordings pre vs. post dose showed no new findings by visual inspection. Results of qEEG analyses using amplitude and coherence measures, pre vs. 6 hours post-dose on Day 14 and Day 28, show increased HF$\alpha$ with active treatment and lower HF$\alpha$ with placebo. This effect is particularly prominent in the left posterior temporal and parietal regions in patients receiving drug and is similar when comparing baseline to Day 14 or 28. Significant univariate effects comparing amplitude from baseline to safety are seen only for changes within the active treatment group. Changes within the placebo group for these measures were not significant.

These findings demonstrate a measurable impact of drug on the qEEG of patients with MDD. The largest effect seen in the active treatment group was HF$\alpha$ in the left posterior temporal region. This finding is consistent with improvement in left temporal lobe function and may also reflect changes in activity in left mesial temporal lobe and hippocampus. Neuropsychological correlates of these changes might include modulating context regulation of affect and clinical response, i.e., fluoxetine, increased alpha activity in posterior regions of the head were associated with clinical response.

EXAMPLE 2

Evaluation by Standard Tests

In this example, the results of the study of Example 1 were evaluated by the efficacy assessments that included the Montgomery-Asberg Depression Rating Scale (MADRS), the Clinician Global Impression-Improvement (CGI-I), the Symptoms of Depression Questionnaire (SDQ) and the Cognitive and Physical Functioning Questionnaire (CPFQ). Despite the minimal improvement observed among the placebo-treated patients, at Day 28, the efficacy measurements appeared to show a clinically meaningful reduction in depressive and cognitive symptoms across all measures for the two lower doses (40 mg/day and 80 mg/day) but not for the highest dose (120 mg/day). However, further analysis showed that the highest dose (120 mg/day) also was effective in improving the condition of these patients. These improvements persisted over time during the follow-up for MADRS, SDQ and CPFQ.

Figure 1A:
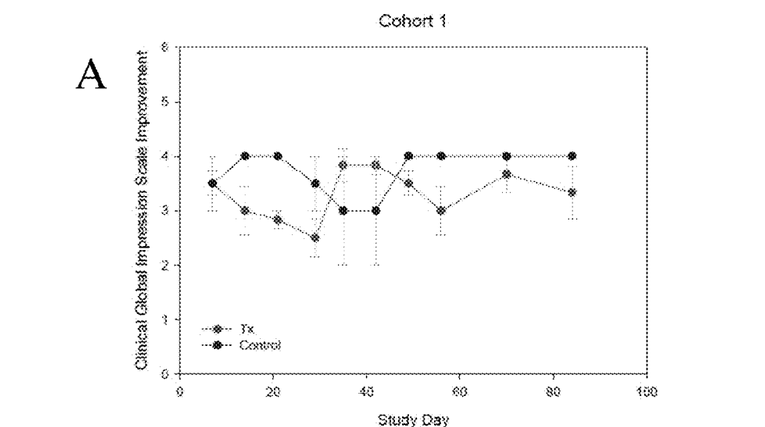
FIGS. 1A, B and C show comparison readings for cohort 1 (40 mg/day), cohort 2 (80 mg/day) and cohort 3 (120 mg/day) on the Clinician Global Impression-Improvement Scale (CGI-I) measure.
Figure 1B:
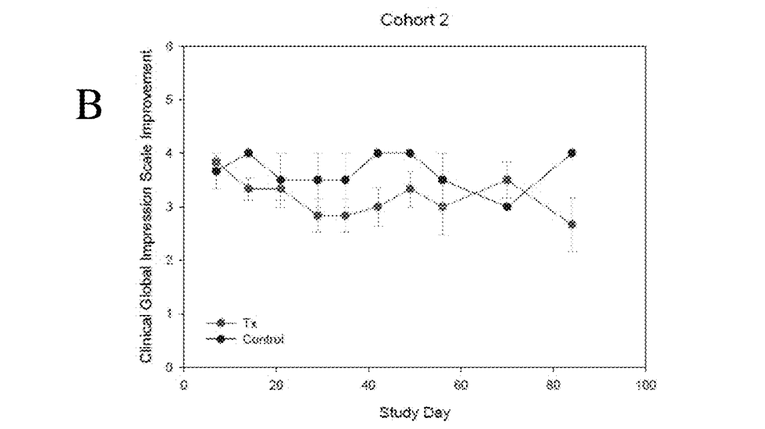
Figure 1C:
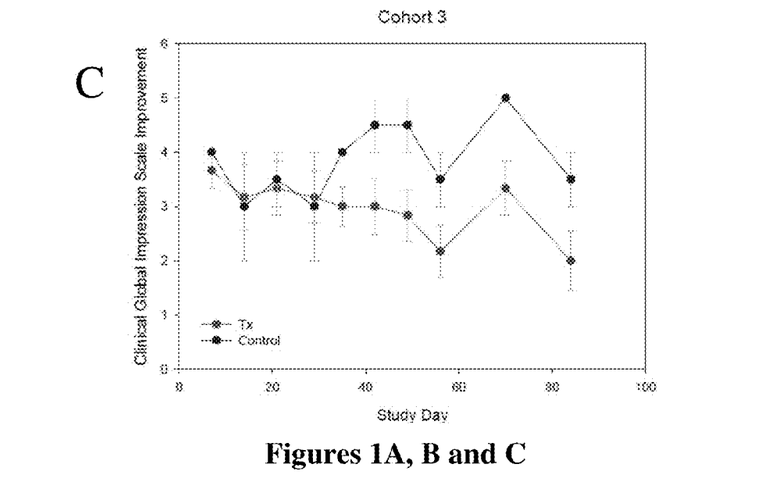

Specifically as shown in FIGS. 1A, B and C, on Day 28, patients administered 40 mg/day of formula (1) showed a CGI-I value of approximately 2.5 as compared to 3.5 for the group containing placebo. Those receiving 80 mg/day (40 mg two times daily) had a value of 3 on the CGI-I while those administered 120 mg/day showed no difference from controls. In this data depiction, each text group (n=6) was compared to a subset of the placebo group (n=2).

Figure 2A:
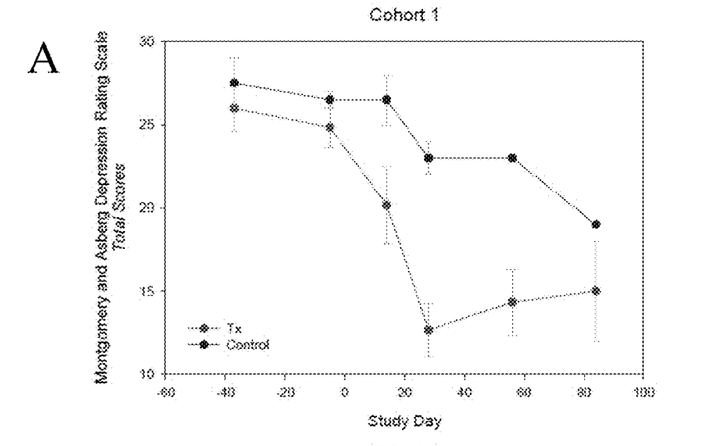
FIGS. 2A, B and C show a comparison of the results on the Montgomery-Asberg Depression Rating Scale (MADRS) for cohorts 1, 2 and 3.
Figure 2B:
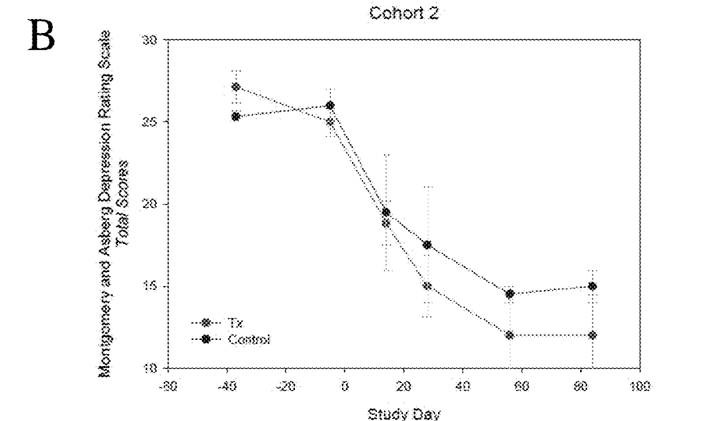
Figure 2C:
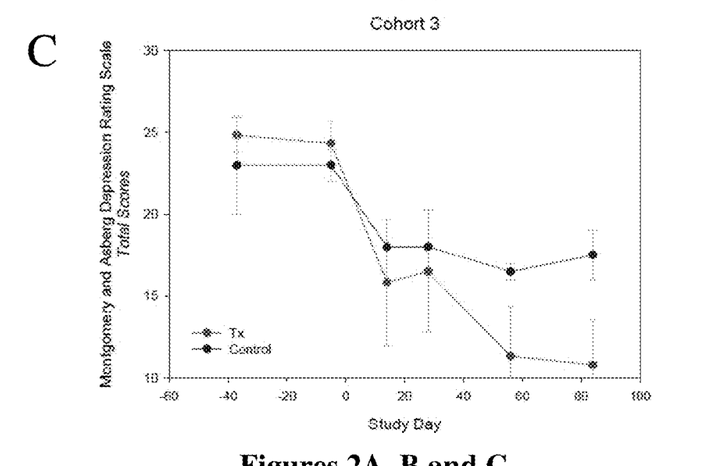

In the MADRS measurement shown in FIGS. 2A, B and C, those receiving 40 mg/day showed a value of 12.5 on this test as compared to 23.5 for the controls. In the group receiving 80 mg/day, a value of 15 on this test was observed as compared to 18 for controls. For those receiving 120 mg/day, the MADRS value was 16 as compared to 18 for controls. Also in this data depiction, each text group (n=6) was compared to a subset of the placebo group (n=2).

Figure 3A:
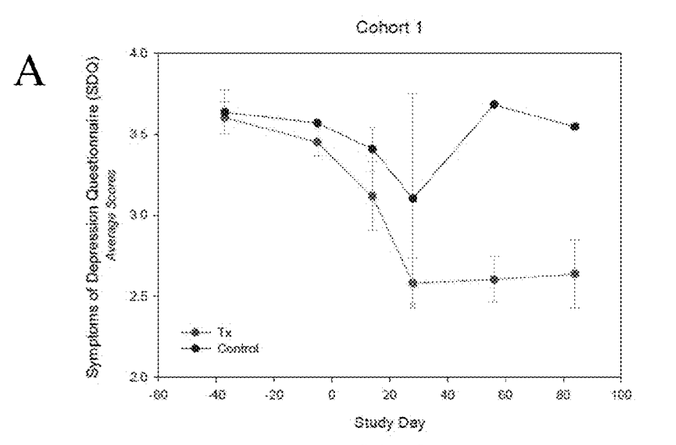
FIGS. 3A, B and C show a comparison of results on Symptoms of Depression Questionnaire (SDQ) for cohorts 1, 2 and 3.
Figure 3B:
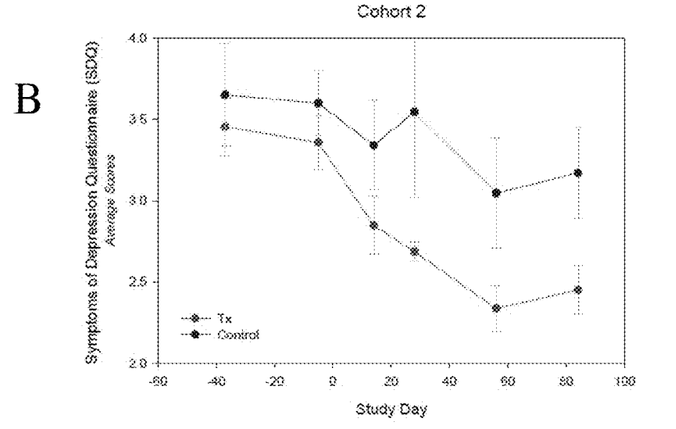
Figure 3C:
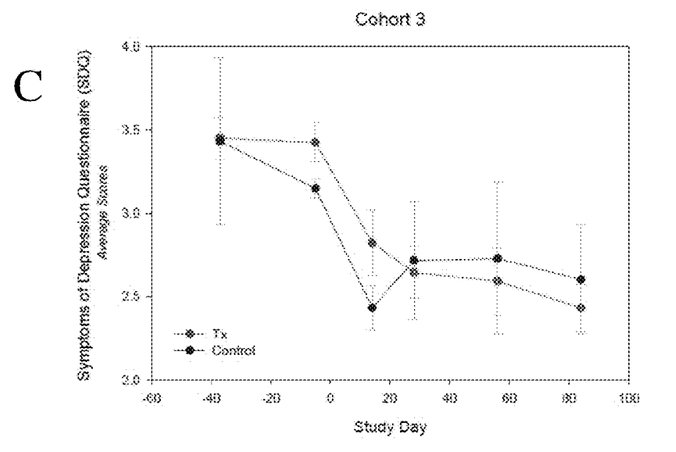

In the SDQ shown in FIGS. 3A, B and C, the patients receiving 40 mg/day scored 2.5 as compared to those taking placebo of 3.1; those taking 80 mg/day showed a value of 2.7 as compared to 3.5 for controls; and in those receiving 120 mg/day, at 28 days their score was actually slightly higher than controls. Also in this data depiction, each text group (n=6) was compared to a subset of the placebo group (n=2).

Figure 4A:
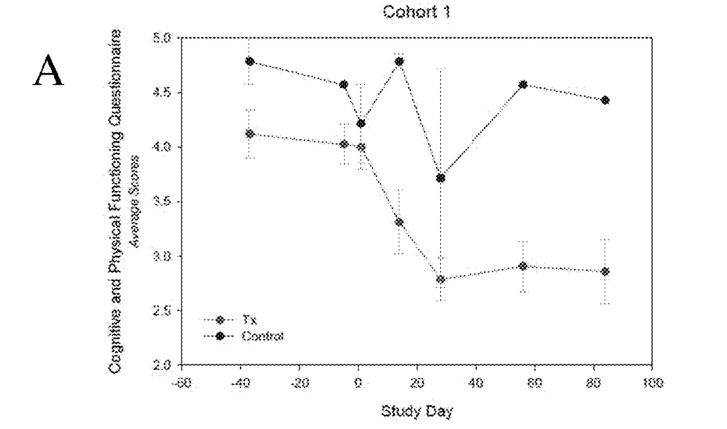
FIGS. 4A, B and C show the results for cohorts 1, 2 and 3 on the Cognitive and Physical Functioning Questionnaire (CPFQ) measure of depression.
Figure 4B:
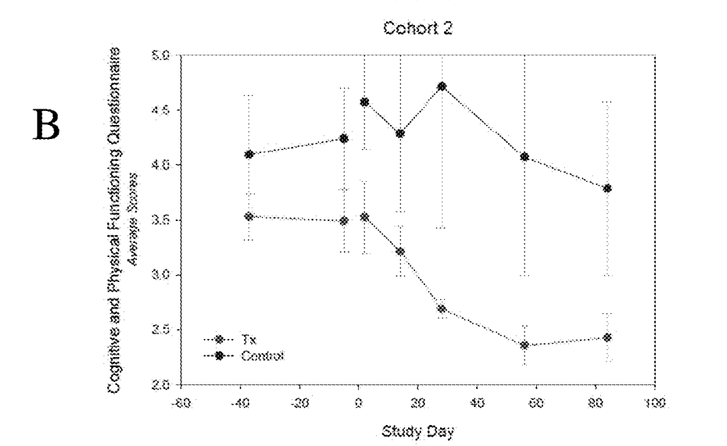
Figure 4C:
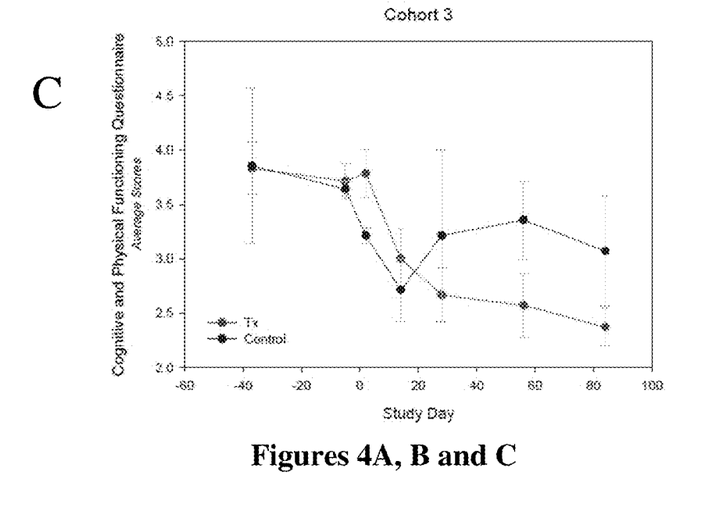

In the CPFQ shown in FIGS. 4A, B and C, the 40 mg/day group gave a value of 2.8 as compared to the control group of 3.75; those receiving 80 mg/day showed a value of 2.6 as compared to controls of 4.6, but those who were given 120 mg/day scored 2.6 as compared to 3.3 for controls. Also in this data depiction, each text group (n=6) was compared to a subset of the placebo group (n=2).

These results were further analyzed by analysis of covariance (ANCOVA). Baseline values were adjusted for initial differences and the results for the placebo group (n=6) and the tested groups (n=18) were collapsed. The sizes of the effects were estimated as Cohen's d group mean differences where d=0.20 indicates only a small difference, d=0.50 indicates a medium difference and d=0.80 indicates a large difference. Cohen's d values are described in Cohen, J. (1988) *Statistical Power Analysis for the Behavioral Sciences* (2nd ed.), Lawrence Erlbaum Associates. D values are used when the scale of a dependent variable is not inherently meaningful, the difference between means are considered in standardized units. That is, effect size is measured in terms of the number of standard deviations by which the means differ. Two commonly used measures are Hedges' g and Cohen's d. Both of these measures consist of the difference between means divided by the standard deviation. They differ only in that Hedges' g uses the version of the standard deviation formula in which division is by N−1, whereas Cohen's d uses the version in which division is by N.

Covariance is a measure of how much two variables change together and how strong the relationship is between them (Lenth, R. V., *The American Statistician* (2001) 55:187-193). Analysis of covariance (ANCOVA) is a general linear model which blends analysis of variance (ANOVA) and regression. ANCOVA evaluates whether population means of a dependent variable (DV) are equal across levels of a categorical independent variable (IV), while statistically controlling for the effects of other continuous variables that are not of primary interest, known as covariates (CV). Therefore, when performing ANCOVA, the DV means are adjusted to what they would be if all groups were equal on the CV. In the CGI-I assay, Day 7 was used as the baseline value; in the remaining assays, Day 0 was used as baseline.

The results of the ANOVA analysis are shown in FIGS. 5A-5D. In these depictions, all members of the placebo group were compared against the compilation of results from all 18 members of the three groups of six administered the different dosages.

Figure 5A:
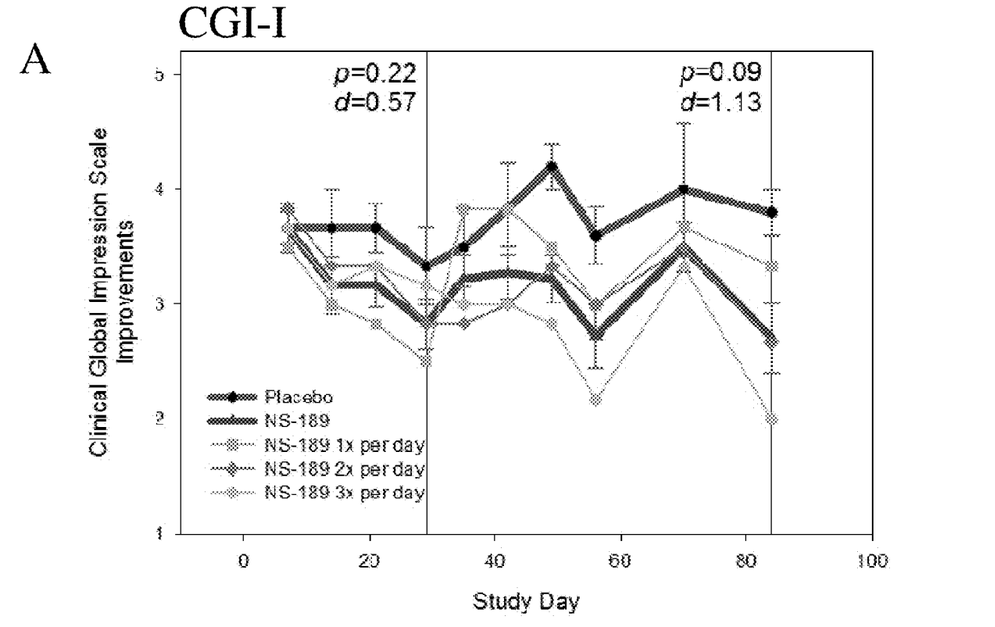
FIGS. 5A, 5B, 5C and 5D show a covariance analysis of the cohorts collectively with respect to placebo on CGI-I, and MADRS, SDQ, and CPFQ measures, respectively.

As shown in FIG. 5A, the ANCOVA analysis showed that collectively for the test groups in the CGI-I test, a d value of 0.57 was obtained at Day 30 and a d value of 1.13 was obtained even as late as 70 days. Table 1 shows the numerical values for the means and standard errors in the CGI-I assay.

TABLE 1

CGI-I Means

| Day | Placebo | SE | Formula (1) | SE | 1x | 2x | 3x |
|---|---|---|---|---|---|---|---|
| 7 | 3.6667 | 0.2108 | 3.6667 | 0.14 | 3.5 | 3.8333 | 3.6667 |
| 14 | 3.6667 | 0.3333 | 3.1667 | 0.2459 | 3 | 3.3333 | 3.1667 |
| 21 | 3.6667 | 0.2108 | 3.1667 | 0.1852 | 2.8333 | 3.3333 | 3.3333 |
| 29 | 3.3333 | 0.3333 | 2.8333 | 0.2177 | 2.5 | 2.8333 | 3.1667 |
| 35 | 3.5 | 0.3416 | 3.2222 | 0.207 | 3.8333 | 2.8333 | 3 |
| 42 | 3.8333 | 0.4014 | 3.2778 | 0.2259 | 3.8333 | 3 | 3 |
| 49 | 4.2 | 0.2 | 3.2222 | 0.207 | 3.5 | 3.3333 | 2.8333 |
| 56 | 3.6 | 0.2449 | 2.7222 | 0.2778 | 3.5 | 3 | 2.1667 |
| 70 | 4 | 0.5774 | 3.5 | 0.2177 | 3.6667 | 3.5 | 3.3333 |
| 84 | 3.8 | 0.2 | 2.7059 | 0.3064 | 3.3333 | 2.6667 | 2 |

Figure 5B:
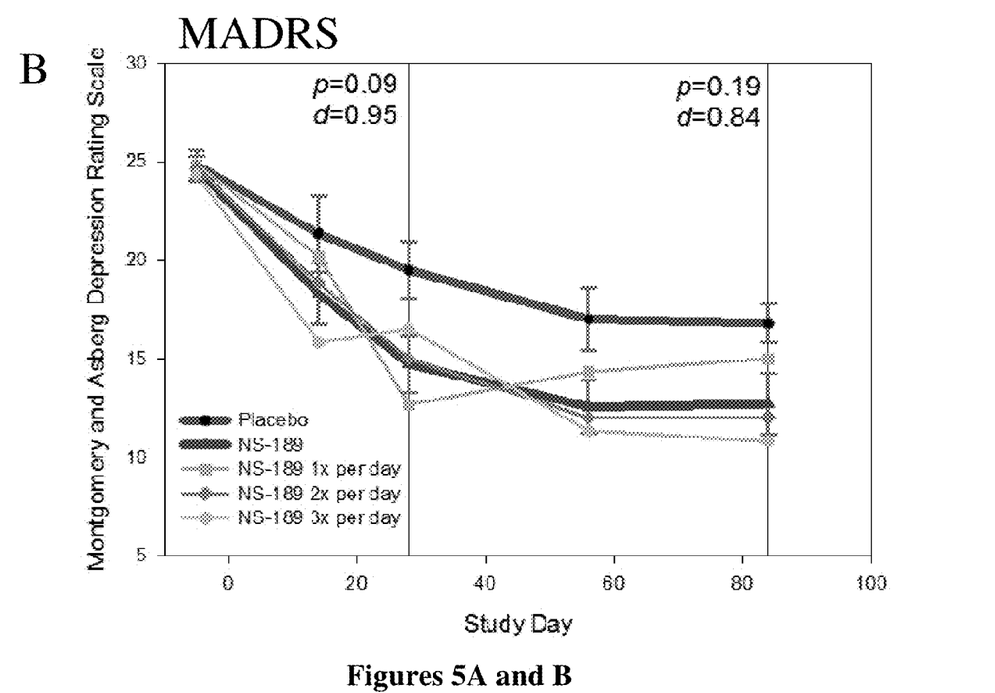

In the MADRS measure, shown in FIG. 5B, at Day 30, the d value was 0.95, and at Day 85, the d value was 0.84. Table 2 shows the numerical values for the means and standard errors in the MADRS assay.

TABLE 2

MADRS Means

| Day | Placebo | SE | Formula (1) | SE | 1x | 2x | 3x |
|---|---|---|---|---|---|---|---|
| −5 | 24.8333 | 0.7032 | 24.6111 | 0.6373 | 24.8333 | 24.6667 | 24.3333 |
| 14 | 21.3333 | 1.9264 | 18.2778 | 1.5441 | 20.1667 | 18.8333 | 15.8333 |
| 28 | 19.5 | 1.4549 | 14.7222 | 1.448 | 12.6667 | 15 | 16.5 |
| 56 | 17 | 1.5811 | 12.5556 | 1.3485 | 14.3333 | 12 | 11.3333 |
| 84 | 16.8 | 0.9695 | 12.7059 | 1.5524 | 15 | 12 | 10.8 |

Figure 5C:
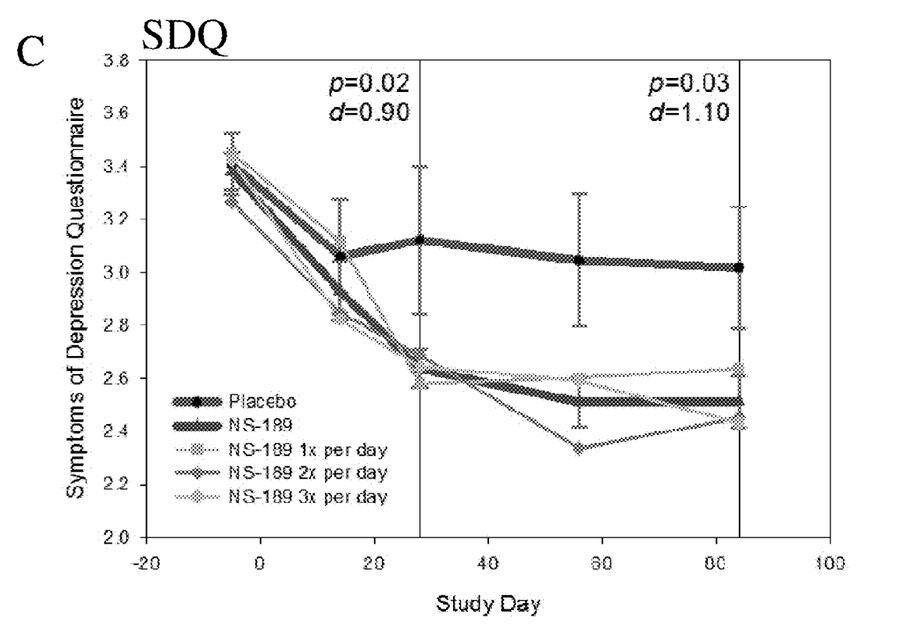

FIG. 5C shows the results of the SDQ measure which gives a d value of 0.90 at Day 30 and a d value of 1.10 at Day 85. Table 3 shows the numerical values for the means and standard errors in the SDQ assay.

TABLE 3

SDQ Means

| Day | Placebo | SE | Formula (1) | SE | 1x | 2x | 3x |
|---|---|---|---|---|---|---|---|
| −5 | 3.4091 | 0.1159 | 3.3801 | 0.0701 | 3.4508 | 3.2652 | 3.4242 |
| 14 | 3.0606 | 0.2171 | 2.9293 | 0.1115 | 3.1174 | 2.8485 | 2.822 |
| 28 | 3.1212 | 0.2783 | 2.6364 | 0.0721 | 2.5795 | 2.6856 | 2.6439 |
| 56 | 3.0455 | 0.2503 | 2.5101 | 0.0928 | 2.6023 | 2.3371 | 2.5909 |
| 84 | 3.0182 | 0.229 | 2.5107 | 0.0966 | 2.6364 | 2.4508 | 2.4318 |

Figure 5D:
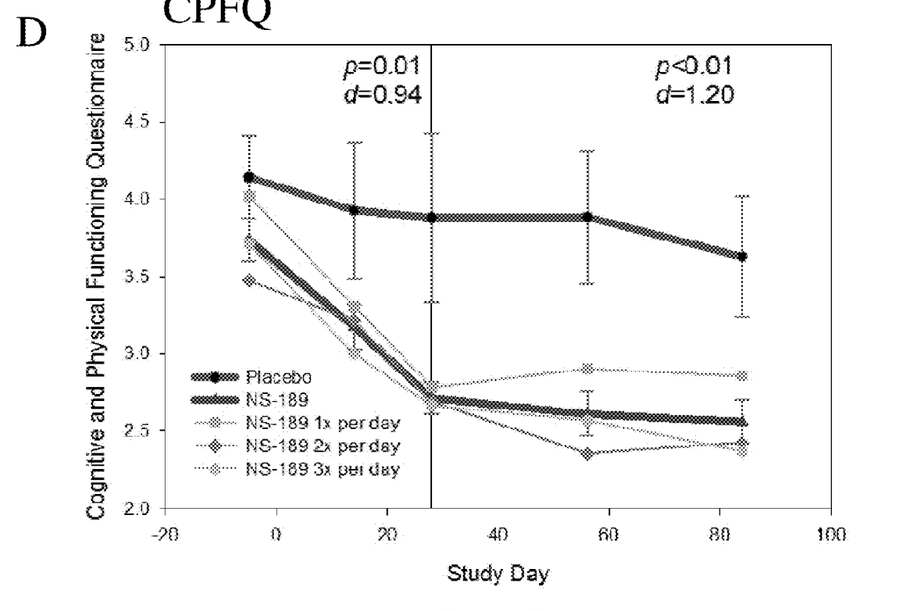

In the CPFQ measure, shown in FIG. 5D, the d value at 30 days was 0.94 and at Day 85 was 1.20. Table 4 shows the numerical values for the means and standard errors in the CPFQ assay.

TABLE 4

| | | | CPFQ Means | | | | |
|---|---|---|---|---|---|---|---|
| Day | Placebo | SE | Formula (1) | SE | 1x | 2x | 3x |
| −5 | 4.1429 | 0.266 | 3.7381 | 0.142 | 4.0238 | 3.4762 | 3.7143 |
| 14 | 3.9286 | 0.4422 | 3.1746 | 0.1468 | 3.3095 | 3.2143 | 3 |
| 28 | 3.881 | 0.5439 | 2.7143 | 0.1039 | 2.7857 | 2.6905 | 2.6667 |
| 56 | 3.8857 | 0.4271 | 2.6111 | 0.1399 | 2.9048 | 2.3571 | 2.5714 |
| 84 | 3.6286 | 0.3902 | 2.563 | 0.1415 | 2.8571 | 2.4286 | 2.3714 |

The highly significant d values indicate the success of the compound. While only the compound of formula (1) was tested in this particular clinical study, in view of the clear similarities of structures between the compound of formula (1) and that of formula (2), similar results are readily predictable for a comparable study using formula (2) as the active compound.

No serious adverse events occurred and the drug was well tolerated. The main limitations of this study are the relatively small sample size of each cohort and the fact that efficacy analyses were not the primary aim, and were meant to be only descriptive in nature. The dramatic and statistically significant results observed in such a small sample are surprising and well beyond expectations.

In summary, a neurogenic compound of formula (1) was successful as a treatment for MDD in a Phase 1B, double-blind, randomized, placebo-controlled, multiple-dose study with three ascending cohorts. In addition to evaluating improvements in cognitive and other related tests for brain function, the hippocampal volume may be measured, for example by MRI, and may be higher for test subjects as compared to placebo, in line with the view that a neurogenesis-based platform can identify promising new treatments for MDD (Fava, M., et al., *J. Psychiatr. Res.* (2012) 46:1553-1563).

The invention claimed is:

1. A method to treat major depressive disorder (MDD) in a human subject, which method comprises administering to a subject diagnosed with MDD an amount of a compound of formula (1) or formula (2)

in the amount of 10 milligrams-130 milligrams per day (mg/day),
wherein said subject is evaluated at the end of administration and after at least one month thereafter.

2. The method of claim 1 wherein the amount of compound administered is 30-100 mg/day.

3. The method of claim 1 wherein the amount of compound administered is 40-90 mg/day.

4. The method of claim 1 wherein the administration is daily over at least 25 days.

5. The method of claim 1 wherein said evaluation comprises administering and evaluating the results of the Montgomery-Asberg Depression Rating Scale (MADRS) and/or the Clinician Global Impression-Improvement Scale (CGI-I), and/or the Symptoms of Depression Questionnaire (SDQ), and/or the Cognitive and Physical Functioning Questionnaire (CPFQ).

6. The method of claim 1 wherein said evaluation comprises performing, and evaluating the results of, quantitative electroencephalogram (qEEG) by observing HFα, wherein an increase in HFα indicates said treating is effective.

7. The method of claim 1 wherein said evaluation comprises analysis of covariance.

8. The method of claim 1 wherein said daily dose is administered once per day, twice per day, or three times per day.

9. The method of claim 1 wherein the compound is administered in an oral dosage form.

10. The method of claim 1 wherein each dose is 10-40 mg of compound.

* * * * *